United States Patent [19]

Aubard et al.

[11] Patent Number: 5,348,980
[45] Date of Patent: Sep. 20, 1994

[54] ENANTIOMERS DERIVED FROM (S)-2-AMINO-2-(3,4-DICHLOROBENZYL)-1-PROPANOL, THEIR USE AND METHOD OF PREPARATION

[75] Inventors: Gilbert Aubard, Palaiseau; Jacques Bure, Neuilly-sur-Seine; Alain Calvet, L'Hay-les-Roses; Claude J. Gouret; Agnés Grouhel, both of Meudon; Jean-Louis Junien, Sevres, all of France

[73] Assignee: Institute de Recherche Jouveinal, Fresnes, France

[21] Appl. No.: 58,698

[22] Filed: May 3, 1993

[30] Foreign Application Priority Data

May 5, 1992 [FR] France .............................. 92 005519

[51] Int. Cl.$^5$ ................... A61K 31/135; C07C 215/00
[52] U.S. Cl. ..................................... 514/653; 564/355
[58] Field of Search ........................ 564/355; 514/653

[56] References Cited

U.S. PATENT DOCUMENTS

| | | | |
|---|---|---|---|
| 4,994,617 | 2/1991 | Aubard et al. | 564/355 |
| 5,245,080 | 9/1993 | Aubard et al. | 564/346 |

FOREIGN PATENT DOCUMENTS 2378746  6/1983  France .

OTHER PUBLICATIONS

U. Schollkpf, Synthesis, p. 969 (1981).

*Primary Examiner*—Richard L. Raymond
*Attorney, Agent, or Firm*—Pennie & Edmonds

[57] ABSTRACT

Enantiomers of (S) configuration of formula (I)

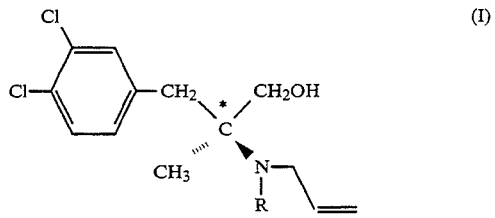

(I)

in which R is H or methyl, with antiallergic and in particular antihistaminic activity, useful as medicinal products.

26 Claims, No Drawings

ENANTIOMERS DERIVED FROM (S)-2-AMINO-2-(3,4-DICHLOROBENZYL)-1-PROPANOL, THEIR USE AND METHOD OF PREPARATION

The present invention relates to new compounds derived from (S)-2-amino-2-(3,4-dichlorobenzyl)-1-propanol, to a process for preparing them and to their therapeutic application.

In U.S. Pat. No. 4,994,617, a description is given of amino alcohols of formula:

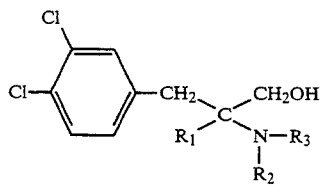

in which:
$R_1$ is lower alkyl,
$R_2$ is H or lower alkyl,
$R_3$ is H, lower alkyl, lower alkenyl, phenyl(lower alkyl) or lower cycloalkylalkyl having from 3 to 6 carbon atoms in the ring, or $R_2$ and $R_3$, together with the nitrogen atom to which they are attached, form a saturated five- to seven-membered heterocycle which can comprise, as a second hetero atom not directly attached to the nitrogen atom, an oxygen, a sulfur or a nitrogen, it being possible for this latter nitrogen hetero atom to bear a $C_1$ to $C_4$ alkyl substituent, the racemic or optically active forms of these amino alcohols and their addition salts with acids.

The products of this invention show both psychotropic and analgesic properties which are especially suitable for the treatment of psychopathological and neuropathological disorders, as well as for painful syndromes of diverse etiologies.

In point of fact, it has now been found that, in the set of particular compounds covered by the general formula of the U.S. Pat. No. 4,994,617, enantiomers of (S) configuration which are new, since they were not synthesized in this patent, possess unexpected antihistaminic and anti-allergic properties which are especially suitable for the treatment of symptomatologies caused by various allergens, and in particular mediated by histamine release.

The present invention relates, by way of new products, to the enantiomers of (S) configuration, according to the rule established by Cahn-Ingold-Prelog, which correspond to the formula I

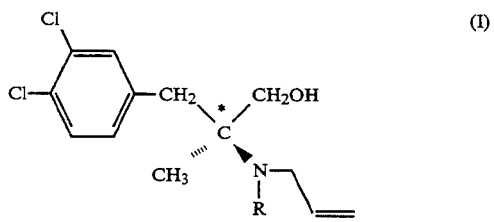

(I)

in which R is hydrogen or a methyl radical, to their addition salts with non-toxic organic or inorganic acids and to their use as an anti-allergic, and in particular antihistaminic, medicinal product.

The addition salts are those obtained with therapeutically acceptable acids, among which there may be mentioned, as examples, acetic, benzenesulfonic, camphorsulfonic, citric, ethanesulfonic, fumaric, hydrobromic, hydrochloric, lactic, maleic, malic, methanesulfonic, nitric, pamoic, phosphoric, salicylic, stearic, succinic, sulfuric and tartaric acids.

The preparation of the salts is carried out by methods familiar to a person skilled in the art, such as the addition reaction of the base of the product (I) with one of the acids, in solution in a water-miscible solvent such as ethanol or acetone or a water-immiscible solvent such as chloroform or dichloromethane, and then to separate the salt formed by concentration and/or cooling of the reaction medium, or alternatively by precipitation of the salt with a solvent in which it is insoluble, such as, for example, diethyl ether.

The invention also relates to a process for preparing the compounds of the invention (I), which consists either in resolving their corresponding racemates which are described in U.S. Pat. No. 4,994,617, or in carrying out the chemical synthesis from precursor enantiomers of (S) configuration.

The process employing resolution of the racemic compounds consists in using an optically active acid to obtain, with the racemic compound treated, either two diastereoisomeric addition salts or two optically active esters, which are separated and from which the enantiomer of (S) configuration which is the subject of the invention and which is also termed "eutomer" in the text, and moreover the antipode of (R) configuration which is considered to be inactive and designated "distomer" in the text, are generated by a suitable treatment. It is also possible to use a method of direct resolution of the racemic compound by high performance liquid chromatography (HPLC). More specifically, these preparations consist in the following: a) as regards the process of resolution by means of diastereoisomeric salts, this consists in reacting the racemic compound, comprising the mixture of eutomer and distomer in equal parts, in a suitable solvent with the optically active acid to form two diastereoisomeric salts, which are separated by their difference in solubility in the solvent used. Under these conditions, the diastereoisomer of lower solubility precipitates and is isolated by filtration.

The separated salts obtained may be recrystallized in selective solvents to obtain a satisfactory optical purity, or else treated, generally in a basic medium, to regenerate the respective enantiomeric amino alcohols. The latter can then be purified by recrystallization, or alternatively subjected to a second step of purification by a fresh formation of diastereoisomeric salts, this optionally being done with an optically active acid different from that used before.

The enantiomers of acids commonly used for the preparation of diastereoisomeric salts according to this process are, to mention non-limiting examples, those of α-phenylglycine, α-phenylalanine and their N-carboxylated derivatives, of malic acid, mandelic acid, tartaric acid and their esterification derivatives with acids, or alternatively camphanic acid, 3-bromo-8-camphorsulfonic acid and its positional isomers, and α-methoxy-α-trifluoromethylphenylacetic acid.

The enantiomers of these acids are commercially available and their use is well known to a person skilled in the art, thereby making them suitable for use in the resolution of racemates comprising the eutomers of formula (I) by preparation and then separation of diastereoisomeric salts, or for the preparation of diastereoisomers for purification of a product previously enriched with respect to a eutomer (I) which is the subject of the invention.

The preparation of the diastereoisomeric salts consists in reacting, per mole of amino alcohol to be separated or purified, from 0.25 to 2.00 mol of the enantiomer of an acid in solution in a solvent or a mixture of solvents which are preferably completely or partially miscible with water, and which are usually chosen from alcohols, ketones, ethers of low molecular weight or alternatively acetonitrile.

Preferably, the reaction is performed in solution in ethanol, methanol or acetone, by reacting from 0.5 to 1.25 mol of the enantiomer of an acid per mole of product to be treated, at a temperature between 20° C. and the boiling point of the solvent employed, this being generally preferred. Salification is complete after a period of between 5 minutes and 3 hours. After this, the reaction mixture is left, first at room temperature and then, where appropriate, at about 0° C., in order to crystallize the less soluble diastereoisomer, which crystallization may be promoted by seeding with a few crystals of the expected salt if it has been prepared already. On completion of crystallization, or at the point considered expedient for obtaining the desired optical purity, the crystallized diastereoisomer is separated by filtration. The two phases each containing a more or less purified diastereoisomer are treated separately, either for purification of the diastereoisomer, or for liberation of the enantiomeric amino alcohol from its salt, this being carried out by an alkaline treatment in an aqueous medium followed by filtration of the enantiomer liberated, or alternatively extraction with a water-immiscible organic solvent. b) alternatively, the resolution of the racemic compound or of the mixture comprising the eutomer (I) consists of an esterification with an optically active carboxylic acid to obtain a mixture of diastereoisomeric esters, which are separated and then saponified to obtain the separate enantiomers of the amino alcohol, including the eutomer (I) and the corresponding distomeric antipode.

According to this process, the racemic or partially enriched compound is subjected to an esterification reaction with an optically pure carboxylic acid or one of its derivatives such as a halide, an anhydride or an ester. The (+) and (−) enantiomers of α-methoxy-α-trifluoromethylphenylacetic acid and their derivatives, for example, are used. The reaction is carried out in an inert solvent which may be chosen from toluene, tetrahydrofuran or alternatively dichloromethane or chloroform, and optionally in the presence of an organic or inorganic base whose role is to catalyze the reaction when the optically active acid derivative employed is an ester, or alternatively to neutralize the acidic by-products formed by the reaction. The catalysts are favorably chosen from sodium and its alcoholates such as sodium methylate, which is preferred, or alternatively from metal alcoholates such as those of aluminum. The bases used for the neutralization can be inorganic, such as alkali metal or alkaline earth metal hydroxides or else the salts of these metals, among which sodium carbonate is preferred, or alternatively organic, for example amines such as trialkylamines, N,N-dialkylanilines or aromatic amines. Among these amines, triethylamine and pyridine are preferred.

The diastereoisomers obtained after reaction are separated and purified by methods familiar to a person skilled in the art, such as fractional crystallization or a chromatographic separation method, and they are then hydrolyzed under the action of a strong base such as an alkali metal hydroxide and usually in an aqueous-alcoholic medium so as to obtain the separated and purified enantiomers of amino alcohols, and more especially, in the context of the invention, the eutomer of (S) configuration of formula (I).

c) the resolution of the racemic compound or the purification of a mixture enriched with respect to a eutomer (I) by high performance liquid chromatography is carried out by separation of the enantiomers on a column containing as stationary phase an acid glycoprotein, termed $\alpha_1$-AGP, immobilized on a porous silica filler the spheres of which have an average diameter of 5 μm-CHIRAL-AGP (R) columns-(Company Chrom Tech).

The mobile phase used for selective elution is a mixture of pH 6 buffer solution (0.01M $KH_2PO_4$ solution adjusted to pH 6 with N KOH) and a water-miscible polar solvent which is chosen from aliphatic alcohols comprising up to three carbon atoms and acetonitrile. The latter solvent and isopropanol are preferred; they are mixed with the buffer solution in the proportion of 0.1 to 25% (v/v) to elute the enantiomers from the stationary phase. The elution is carried out under conditions suited to the good separation of the isomers, namely a temperature of between 10° and 40° C. and a flow rate compatible with the resistance of the material used but which can reach the point of producing a pressure of the order of $10^7$ Pa.

However, the preferred methods for preparing the enantiomers of (S) configuration (I) are those employing precursor enantiomers of (S) configuration according to the rule established by Cahn-Ingold-Prelog.

The preferred process consists in reacting an allyl halide with a precursor amino alcohol of (S) configuration, of formula:

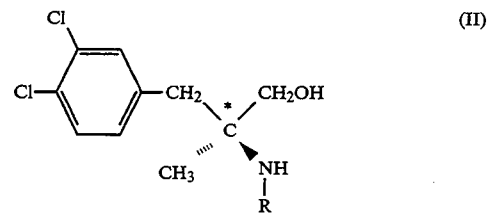

(II)

An alternative process consists in reducing, with a complex hydride derived from boron or from aluminum, the carbonyl function of a precursor amino ester of (S) configuration, of formula

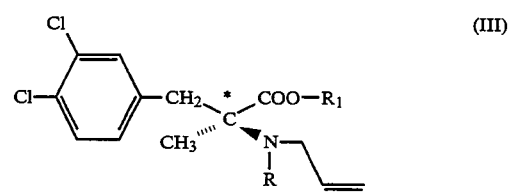

(III)

in which R is hydrogen or methyl and $R_1$ is hydrogen or a lower alkyl radical such as methyl or ethyl.

As regards the (S) configuration of the compounds of the invention and the precursors (II) and (III), this was assigned by analogy to that of a precursor which is common to them, methyl (S)-(−)-3-(3,4-dichlorophenyl)-2-methylalaninate of formula (IV)

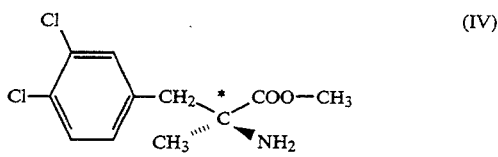

(IV)

the enantioselective synthesis of which was carried out according to the process described by U. Schöllkopf (Synthesis, p. 969, 1981), and which consists in alkylating (2R,5SR)-(−)-2,5-dihydro-3,6-dimethoxy-2-isopropyl-5-methylpyrazine (Merck product-ref. 818314) with 3,4-dichlorobenzyl chloride, and then in carrying out an acid hydrolysis of the (2R,5S)-5-(3,4-dichlorobenzyl)-2,5-dihydro-3,6-dimethoxy-2-isopropyl-5-methylpyrazine to obtain the methyl ester of formula (IV) which, on N-alkylation with an allyl halide, yields the precursor (III) in which R is hydrogen, or on reduction with an organometallic hydride yields the precursor (II) in which R is hydrogen or methyl, to obtain a eutomer (I).

The process for preparing the compounds (I) of the invention which is especially preferred consists in:
- reacting an allyl halide with an amino alcohol (II) in which R is hydrogen, to prepare a eutomer (I) of the invention in which R represents hydrogen,
- and then carrying out a methylation of this eutomer (I) with formaldehyde and formic acid to obtain the eutomer (I) of the invention in which R represents a methyl radical.

The implementation of this process consists in: - reacting (S)-(−)-2-amino-2-(3,4-dichlorobenzyl)-1-propanol, a compound described in Example 1C of the U.S. Pat. No. 4,994,617, with an allyl halide such as chloride or iodide or, preferably, allyl bromide, in an inert solvent such as toluene or acetonitrile. Optionally, a basic agent, inorganic such as sodium carbonate or else organic such as triethylamine, is added to the reaction medium in order to promote the reaction. In practice, from 0.5 to 1.5 mol of allyl halide is used per mole of amino alcohol employed, the reaction being carried out in solution in 2 to 3 liters of the chosen solvent. Depending on the solvent and the halide used, a satisfactory result is obtained after a reaction period of between 1 and 24 hours for temperature conditions of between 20° and 110° C. The preferred conditions, using allyl bromide, are from 2 to 5 hours for a reaction temperature of between 40° and 100° C., the amino alcohol (I) obtained being isolated and purified by familiar methods, in particular by fractional crystallization, and then by carrying out the N-methylation of this compound (I) obtained as described above.

To this end, a reductive methylation reaction is carried out with an aqueous formaldehyde solution and formic acid according to the Eschweiler-Clarke process.

Per mole of amino alcohol (I) to be N-methylated, a quantity of aqueous solution corresponding to 1.2 to 3.5 mol of pure formaldehyde and from 2 to 5 mol of pure formic acid is employed.

In practice, the formaldehyde is added first to the product, and then, after an exothermic reaction, addition of the formic acid is performed and the reduction reaction is carried out by heating the mixture for 1 to 2 hours at 90°–100° C.

After treatments, the eutomer (I) in which R is methyl is purified by conventional, in particular chromatographic, methods.

As regards the preparation of (S)-(−)-2-amino-2-(3,4-dichlorobenzyl)-1-propanol, the state of the art is taught in French Patent No. 2,378,746, Example 2-d, for the synthesis of levorotatory 1-3-(3,4-dichlorophenyl)-2-methylalanine in 5 steps from methyl 2-isocyanopropionate and 3,4-dichlorobenzyl bromide, and furthermore, in U.S. Pat. No. 4,994,617, Example 1-C, where the reduction of this acid with the boranedimethyl sulfide complex is taught.

Advantageously, compared to this preparation which comprises six steps in all, the preferred process for the purposes of the invention, which is faster and more economical, enables (S)-(−)-2-amino-2-(3,4-dichlorobenzyl)-1-propanol to be prepared in four synthesis steps from 3,4-dichlorophenylacetone. Essentially, the process consists in reacting the ketone by the Bucherer-Berg reaction with potassium cyanide and ammonium carbonate to obtain (+/−)-5-(3,4-dichlorobenzyl)-5-methylhydantoin, which is subjected in an alkaline aqueous-acetone medium to a stereospecific salification with (R)-(+)-α-methylbenzylamine so as to obtain the addition salt thereof with the (S)-(−) enantiomer of the hydantoin, which, being insoluble, is filtered off, and from which (S)-(−)-5-(3,4-dichlorobenzyl)-5-methylhydantoin is obtained in a state of optical purity greater than 98% by treatment in an acid solution.

The (S) enantiomer of this hydantoin is hydrolyzed in a conventional manner in an alkaline aqueous medium to obtain (S)-(−)-2-(3,4-dichlorobenzyl)alanine, which is reduced as described in Example 1 of U.S. Pat. No. 4,994,617 with the borane-dimethyl sulfide complex to obtain (S)-(−)-2-amino-2-(3,4-dichlorobenzyl)-1-propanol.

These preferred preparation processes are illustrated by the preparation and the examples described below.

Preparation: (S)-(−)-2-amino-2-(3,4-dichlorobenzyl)-1-propanol [(II); R=H]

- Stage 1: (+/−)-5-(3,4-dichlorobenzyl)-5-methylhydantoin 160.0 g (0.79 mol) of 3,4-dichlorophenylacetone in 700 ml of ethanol are introduced into a reactor, and the mixture is heated to 40° C. to obtain dissolution. 53.0 g (0.81 mol) of potassium cyanide, 149.0 g of ammonium sesquicarbonate and 700 ml of water are then added.

The mixture is heated with stirring to a temperature of between 65° and 70° C. for 15 hours. The suspension is cooled with stirring to 10°–15° C. and left for 16 hours at this temperature. The insoluble matter is filtered off and washed with water and then with diisopropyl ether before being dried under vacuum at 50° C. to constant weight.

Weight obtained 155.0 g, Yld 72%, M.p. 240° C.

- Stage 2: (S)-(−)-5-(3,4-dichlorobenzyl)-5-methylhydantoin 100 ml of demineralized water are mixed with 150 ml of acetone in a reactor set up in the reflux position, and 3.7 g (0.091 mol) of sodium hydroxide pellets are then added.

50.0 g (0.183 mol) of the racemic hydantoin obtained in the preceding stage and 22.2 g (0.183 mol) of (R)-(+)-α-methylbenzylamine are then added successively.

With stirring, the mixture is brought to reflux until the reactants have dissolved. 100 ml of water are then introduced while heating the mixture gradually to 70°

C., and the solution is thereafter cooled slowly with stirring.

Crystallization starts to be seen at about 60° C. and the mixture is then maintained for 1 h 30 min at 50° C. in order to complete the crystallization and thereafter cooled to approximately 20° C. for 30 minutes.

The crystalline precipitate is filtered off and washed with twice 100 ml of a 2:1 (vol/vol) acetone/water mixture.

The insoluble matter is suspended without further treatment in 250 ml of water, and the mixture is acidified to pH 1 by the gradual addition of concentrated hydrochloric acid solution (d=1.18).

The insoluble matter is filtered off and washed with water. The optical purity of the product, determined by HPLC on an aliquot fraction, is 98.6%.

The wet product is recrystallized under reflux in 200 ml of a 1:1 (vol/vol) water/acetone mixture.

After cooling to 15° C. for two hours, the insoluble matter is filtered off, washed with an acetone/water mixture and then dried under vacuum at 50° C.

18.79 g of S-(—)-5-(3,4-dichlorobenzyl)-5-methylhydantoin are obtained.

Yield=75%, Optical purity=100% (HPLC)
M.p. 276° C., $[\alpha]_D^{20}=28.4°$ (c=1, EtOH)

- Stage 3: (S)-(—-)-2-(3,4-dichlorobenzyl)alanine 4.7 g (115 mmol) of sodium hydroxide pellets are dissolved in 25 ml of water in an autoclave. 7.0 g (25.6 mmol) of the (S)-(—)-hydantoin prepared in Stage 2 above are added. After the apparatus is hermetically sealed, the mixture is heated with stirring for 8 hours to 140°–145° C. under a pressure of 3 to 4 bars.

After cooling to 20°–25° C., the chestnut-brown solution which is obtained is acidified with stirring with concentrated hydrochloric acid solution to pH 5.8–6.2. After cooling to 10° C. for 30 minutes, the insoluble matter is filtered off, washed with water and then with toluene and dried under vacuum at 80° C.

Weight=5.5 g, Yld=86%
$[\alpha]_D^{20}=6.9°$, (c=1.5, CH$_3$OH),

- Stage 4: (S)-(—)-2-amino-2-(3,4-dichlorobenzyl)-1-propanol 62.5 ml of tetrahydrofuran (THF) and then 2.48 g (10 mmol) of (S)-(631 )-2-(3,4-dichlorobenzyl)-alanine are introduced into a reactor protected from moisture and under a nitrogen atmosphere. 3.80 g (50 mmol) of borane-dimethyl sulfide complex (BMS) are added dropwise, in the course of 30 minutes and at a temperature of 20° C. to the suspension obtained. Stirring is maintained for 15 minutes at room temperature and the mixture is then heated to reflux for 4 hours 30 minutes. After cooling to 5° C., 7.5 ml of methanol are introduced gradually without exceeding 20° C., followed, in an identical manner, by 7.5 ml of N sodium hydroxide solution. The suspension obtained is left overnight, and the insoluble matter is filtered off and removed. The filtrate, evaporated under vacuum and on a water bath, gives a white residue which is taken up with 50 ml of water. The mixture is acidified to pH 1 by adding concentrated hydrochloric acid (d=1.18).

The solution obtained is extracted with twice 15 ml of ether. The ether phases are discarded, and the acid phase is alkalinized in the cold state to pH 12 by adding concentrated sodium hydroxide solution (d=1.38) and then saturated with sodium chloride.

The alkaline mixture is extracted with 3 times 20 ml of ether, and the combined ether phases are washed with saturated sodium chloride solution and then dried.

After evaporation of the ether, the amino alcohol is obtained in the form of a white and amorphous solid residue.

Weight 2.10 g, M.p. 86° C., Yld=90%
$[\alpha]_D^{20}=-1.820$, (c=5; CH$_3$OH [lacuna]

Example 1 -
(S)-(—)-N-allyl-2-amino-2-(3,4-dichlorobenzyl)-1-propanol [(I); R=H]

35.0 g (0.15 tool) of (S)-(—)-2-amino-2-(3,4-dichlorobenzyl-1-propanol, $[\alpha]_D^{20}=-1.8°$ (c=5, methanol), are dissolved in 350 ml of anhydrous acetonitrile in a reactor protected from moisture.

12.9 ml (18.08 g–0.15 mol) of allyl bromide are added to the solution with stirring at 20°–25° C. and in the course of approximately 5 minutes. The solution is kept stirring for one hour at the same temperature and then heated gradually to 50°–60° C. This temperature is maintained for two and a half hours, during which period a precipitate appears. The suspension is then cooled with a bath of ice-cold water at 5° C. The precipitate is then filtered off, taken up with 800 ml of water, alkalinized to pH 11 with 10 N sodium hydroxide solution and extracted with 3 times 250 ml of diethyl ether.

The combined ether phases are extracted with saturated NaCl solution and then dehydrated over Na$_2$SO$_4$. The ether is evaporated off under vacuum and on a water bath. The crude solid residue is taken up for dissolution in 500 ml of hexanes under reflux. After cooling, the crystalline white precipitate of purified (S)-(—)-N-allyl-2-amino-2-(3,4-dichlorobenzyl)-1-propanol is filtered off and then brought to constant weight in an oven at 40° C. under vacuum.

Weight: 25.4 g, M.p.=87°–88° C. Yld 62%
$[\alpha]_D^{20}=-12°$ (c=0.5, N HCl)
Note: observed deviation not significant for:
(c=5, C$_2$H$_5$OH) and (c=1, C$_2$H$_5$OH/N HCl)
-$^1$H NMR (CDCl$_3$ TMS): δ (ppm) 1.00 (s, 3H); 1.00–2.90 (m, 2H exch. D$_2$O); 2.65 (s, 2H); 3.10–3.40 (m, 4H); 5.00–5.35 (m, 2H); 5.65–6.15 (m, 1H); 6.90–7.45 (m, 3H).

Example 2 -
(S)-(+)-N-allyl-2-methylamino-2-(3,4-dichlorobenzyl)-1-propanol [(I); R=CH$_3$]

13.5 g (49 mmol) of the (S)-N-allylaminopropanol prepared in Example 1 above are mixed with 13.5 ml of 37% w/v formaldehyde solution (equivalent to 5.0 g-133 mmol) in a reactor equipped with a powerful stirrer.

The mixture is warmed to about 40°–50° C. to promote homogenization with stirring, and then cooled to 15° C. 9.3 ml of 100% formic acid (d=1.22, equivalent to 11.35 g-247 mmol) are then added dropwise. The clear solution obtained is maintained for two and a half hours with stirring on a boiling water bath. After cooling, 200 ml of water are added, and the mixture is acidified to pH 1 by adding concentrated hydrochloric acid and extracted with 3 times 100 ml of diethyl ether. The ether phases are discarded, the acid phase is alkalinized to pH 11 with 10 N sodium hydroxide solution without exceeding 25° C. and the mixture is then extracted with 3 times 150 ml of ether.

The combined ether phases are washed with NaCl solution and then dried over Na$_2$SO$_4$. The ether is evaporated off, and the crude residue of 14.0 g is purified according to the so-called "Chromatoflash" chromatographic technique on a column packed with silica.

Elution with a 95:5 (v/v) dichloromethane/methanol mixture enables purified (S)-(+)-N-allyl-2-methylamino-2-(3,4-dichlorobenzyl)-2-propanol to be obtained in an oily form, which crystallizes slowly to a product of low melting point.

Weight = 11.5 g, Yld = 81%

$[\alpha]_D^{20} = +13°$ (C = 1, N HCl)

$^1$H NMR (CDCl$_3$-TMS): δ (ppm) 0.95 (s, 3H); 2.30 (s, 3H); 2.70 (s, 2H); 2.95 (s; 1H exch.D$_2$O); 3.05–3.45 (m, 4H); 5.00–5.35 (m, 2H); 5.60–6.05 (m, 1H); 6.95–7.40 (m, 3H)

- HPLC - Determination of the optical purity on a "Chiral-AGP (R)-supplier Chromtech" column, eluting with a mixture comprising 0.01M KH$_2$PO$_4$ adjusted to pH 6 and Isopropanol - (v/v)

result: % purity > 98

- Hydrochloride: the eutomer (I) obtained above is dissolved in 150 ml of dichloromethane. While maintaining a temperature below 25° C., an excess of ethereal hydrogen chloride is added to the solution, and the mixture is then left stirring for 1 hour while protected from moisture.

The solvents are evaporated off under vacuum and on a water bath. The solid residue is dissolved in the minimum quantity of methanol at 20°–25° C., and the purified hydrochloride is obtained by precipitation after adding anhydrous diethyl ether.

M.p. 171°–172° C.

- Elemental analysis (C$_{14}$H$_{20}$Cl$_3$NO = 324.69)

Calculated C 51.79 H 6.21 Cl 32.76 N 4.31 O 4.93
Found C 51.71 H 6.30 Cl 32.72 N 4.20 O 5.22

- IR (KBr): 3250, 2600, 1470, 1400, 1060, 1030, 950, 830 cm$^{-1}$

The distomeric antipodes of the compounds presented in Examples 1 and 2 are, respectively:

- (R)-(+)-N-allyl-2-amino-2-(3,4-dichlorobenzyl)-1-propanol

M.p. 89° C. $[\alpha]_D^{20} = +11°$ (c=0.5, N HCl)

- (R)-(−)-N-allyl-2-methylamino-2-(3,4-dichlorobenzyl)-1-propanol

M.p. < 50° C. $[\alpha]_D^{29} = -14°$ (c=1, N HCl)

They were prepared according to the procedure described in the above examples, from (R)-(−)-2-amino-2-(3,4-dichlorobenzyl)-1-propanol described in Example 1 B of U.S. Pat. No. 4,994,617.

The low toxicity of the products of the invention and the unexpected pharmacological properties which have been discovered justify the value of the compounds in preventive or curative treatments of allergic manifestations, and in particular of those caused by histamine release.

The acute toxicity of the compounds (I) was studied orally in male mice. To this end, the products were administered in aqueous solution on the basis of 2 ml per 100 g of body weight. The animals were observed during the three hours following administration, and then daily for 14 days, after which they were sacrificed and autopsied.

The LD$_{50}$ values (lethal doses causing the death of 50% of the animals) are in the region of 1,000 mg/kg, which may be perceived as a relatively low toxicity of the products.

The anti-allergic properties of the eutomers (I) were demonstrated by their capacity to inhibit, in guinea pigs sensitized to ovalbumin, an anaphylactic bronchoconstrictor effect produced by an aerosol containing this same allergen.

The technique performed consists in previously sensitizing guinea pigs weighing 250 to 300 g by two intraperitoneal injections, separated by an interval of 24 hours, of 0.5 ml of a sterile suspension of physiological saline (0.9% NaCl) containing 20 μg of ovalbumin (Grade V; Sigma) and 100 mg of aluminum hydroxide Al(OH)$_3$.

At the same time, unsensitized control animals are treated with two injections of suspension not containing ovalbumin.

The actual experiment is performed after a period needed for the sensitization of the animals, which is between 14 and 21 days. It is generally arrived at after 18 days, and consists in first administering increasing quantities of the test product in solution in water orally to groups of 5 animals, on the basis of 0.5 to 1.0 ml per animal, corresponding to doses of 1 to 10 μmol/kg of product.

The animals are then anesthetized 50 minutes after this administration by an intraperitoneal injection of a solution of urethane. They then undergo a surgical preparation which consists in:
- placing a cannula in the left carotid in order to be able to determine the blood pressure and heart rate in continuous fashion,
- placing a cannula in the right jugular vein for the intravenous administration of solutions,
- after an upper cervical tracheotomy, inserting a polystyrene cannula (internal diameter 2.65 mm, length 9 to 11 mm) in order to ventilate the animal (Harvard 50–1728 pump; Kent - Great Britain) at a frequency of 60 insufflations per minute and on the basis of a volume of 1.2 ml/kg each.

After this operation, and stabilization of the intratracheal pressure and the blood pressure, an aerosol of ovalbumin is administered by means of an ultrasonic nebulizer (Pulmosonic apparatus; model 2511). The apparatus delivers 30 insufflations in 30 seconds via the tracheal ventilation in a total volume of 30 μl of an ovalbumin suspension containing 5 mg/ml. After 60 minutes, the intratracheal pressure measured in mm of Hg is determined for each animal of the test groups and those of the control group. These measurements enable the extent of the inhibition of bronchoconstriction produced by the test product to be determined. The results are expressed as the ED$_{50}$ of the product, which is the effective dose, expressed in micromols per kg (μmol/kg) capable of inhibiting 50% of the bronchoconstriction caused by ovalbumin in the sensitized animal under the conditions of the test.

Determined under these conditions, the inhibitory ED$_{50}$ of the hydrochloride of the eutomer (I) of Example 2 is 1.84 μmol/kg).

Furthermore, the antihistaminic properties were studied in guinea pigs by the bronchoconstriction test performed according to the method of H. Konzett and R. Rossler (Arch. Exp. Path. Pharmak.—Naunym Schmiedeberg - 195, 71–74, 1940).

The products of the invention were studied in this test after administration in solution or in suspension via the intravenous and intraduodenal routes, and also in powder form via the intranasal route.

Irrespective of the administration route, the preparation of the animals employed in the test consists in first anesthetizing male guinea pigs weighing 350 to 400 g by intraperitoneal (i.p.) injection of a sterile and isotonic solution containing 25% (w/v.) of ethyl carbamate on the basis of 6.0 ml/kg, and in then fitting the animals with a tracheal cannula to permit measurement of the pulmonary pressure, a cannula in the right jugular vein for the intravenous (i.v.) administration of solution, and also a cannula in the left carotid artery for qualitative observation of the blood pressure.

The animals are then connected to a pump (Harvard, ref. 50-1718) in order to maintain an artificial ventilation at a frequency of 60 insufflations per minute; the intratracheal pressure is recorded by an assembly comprising a transducer, an amplifier and a recorder (Gould, respective refs.: PLOEZ, 13-4615-50 and 8188-G4400-06).

Fitted in this way, the animals are left undisturbed for 10 minutes before the beginning of the actual experiment, which is carried out in different ways according to the administration route envisaged.

a) i.v. administration

In base form, the test products are dissolved in an isotonic solution (0.9% NaCl) containing 10% (v/v) of Transcutol (R). Dilutions are performed by adding isotonic solution. In salt, in particular hydrochloride, form, the solutions are prepared in the isotonic solution.

The treatment of the animals consists of a series of administrations of histamine dihydrochloride solution on the basis of 100 μmol/kg before and after treatment with the solution of test product, which is carried out according to the following time schedule:

t = −20 minutes - histamine (100 μmol/kg)
t = −10 minutes - ditto control
t = 0 - injection of the test product
t = +10 minutes - histamine (100 μmol/kg)
t = +20 minutes - ditto
t = +30 minutes - ditto
t = +40 minutes - ditto
t = +50 minutes - ditto
t = +60 minutes - ditto The results of the tests are presented in Table 1.

b) i.d. administration

In base form, the test products are suspended in a solution containing 1% w/v of carboxymethylcellulose (CMC), and, in salt form, they are dissolved in an isotonic solution before being administered via a cannula whose end is placed in the animal's duodenum.

The time schedule for the successive administrations of histamine via the i.v. route and that for the test solution via the i.d. route are identical to that described above in a).

The results of these tests are presented in Table 2.

c) intranasal-powder (In.p) administration

The test product is administered via a nasal insufflation of a powder consisting of 20 mg of lactose loaded with the appropriate quantity of the test product. Before this insufflation, the artificial ventilation of the animal is momentarily stopped in order to facilitate the pulmonary penetration of the compound. The time schedule for the administration of histamine via the i.v. route and that of the test product via the In.P. route is as follows:

t = −15 minutes - histamine (100 μmol/kg)
t = −5 minutes - ditto control
t = 0 minutes - insufflation test product
t = 5 minutes - histamine (100 μmol/kg)

The results of these tests are presented in Table 3.

- Calculation and expression of the results:

For each administration route and for each time of administration of histamine, the activity of the products is expressed as the percentage change in amplitude of bronchoconstriction, calculated relative to that produced by the "control" administration of histamine which precedes the administration of the test product. The % change is calculated according to the formula:

$$\% \text{ change} = 100 - \left( \frac{Bc(tx) - Bo(tx)}{Bc(to) - Bo(to)} \times 100 \right)$$

in which:

$Bc(tx)$ represents the amplitude of the bronchoconstriction in mm at time x,
$Bo(tx)$ the amplitude of the base-line respiration in mm at time x,
$Bc(to)$ and $Bo(to)$ the corresponding amplitudes in mm on receipt of the "control" administration of histamine which precedes that of the test product.

The inhibitory activity of the test products on histamine-induced bronchoconstriction is expressed at different times of the studies as their $ED_{50}$, which is the effective dose of product, expressed in μmol/kg, capable of inhibiting 50% of the histamine-induced bronchoconstriction at the time in question.

Failing this expression, the results are expressed as a % change at the time in question and for a given concentration of the test product. Under these conditions, a positive percentage corresponds to a potentiating effect on bronchoconstriction and, conversely, a negative percentage to an inhibitory effect.

Statistical analyses of the results were carried out by the Student t test. A value of $p < 0.05$ is considered significant.

The compounds of the invention described in Examples 1 and 2 were employed in these tests. In addition, as a comparative product for the eutomer of Example 1, the racemic (R,S) compound corresponding to it, and which is described and prepared in Example 7 of U.S. Pat. No. 4,994,617, was employed. As regards the eutomer of Example 2 and its hydrochloride, the hydrochloride of the racemic (R,S) compound which is also the corresponding distomeric antipode of (R) configuration prepared as described above, were employed comparatively in these tests.

Fenspiride (INN) hydrochloride, known as an antagonist of allergens which are active on the airways, and Cromakalim (INN), which is a compound known to be a bronchodilator, were also employed in these tests as reference compounds.

TABLE 1

Inhibitory effect, via the i.v. route, on bronchoconstriction caused by 100 μmol/kg of histamine
Tests via the i.v. route (Results: $ED_{50}$ μmol/kg)

| COMPOUND | Config. | t = 10' | t = 20' | t = 30' | t = 40' | t = 50' | t = 60' |
|---|---|---|---|---|---|---|---|
| Example 1 of the invention | (S) | 4.89 | 2.88 | 2.54 | 2.58 | 3.17 | 3.55 |
| Comparative racemate | (R, S) | 6.65 | 4.10 | 4.38 | 3.39 | 3.02 | 3.52 |
| Example 2 of the invention | | | | | | | |

TABLE 1-continued

Inhibitory effect, via the i.v. route, on bronchoconstriction caused by 100 μmol/kg of histamine
Tests via the i.v. route (Results: ED$_{50}$ μmol/kg)

| COMPOUND | Config. | t = 10' | t = 20' | t = 30' | t = 40' | t = 50' | t = 60' |
| --- | --- | --- | --- | --- | --- | --- | --- |
| base | (S) | 1.27 | 0.93 | 0.74 | 0.96 | 1.01 | 0.76 |
| hydrochloride | (S) | 1.68 | 0.70 | 0.58 | 0.57 | 0.51 | 0.53 |
| Comparative racemate. HCl | (R, S) | 3.72 | 2.11 | 1.88 | 2.07 | 2.34 | 2.22 |
| Comparative distomer* | (R) | +6.3 | +18.4 | +28.2 | +35.4 | +36.7 | +41.1 |
| Reference: |  |  |  |  |  |  |  |
| Fenspiride (INN). HCl | — | 4.25 | 4.99 | 6.26 | 8.90 | 8.01 | 11.03 |

*% potentiating effects on bronchoconstriction statistically non-significant for 3.5 μmol/kg.

TABLE 2

Inhibitory effect, via the i.d. route, on bronchoconstriction caused by 100 μmol/kg of histamine
test via the i.d. route (Results: ED$_{50}$ μmol/kg)

| COMPOUND | Config. | t = 10' | t = 20' | t = 30' | t = 40' | t = 50' | t = 60' |
| --- | --- | --- | --- | --- | --- | --- | --- |
| Example 1 of the invention | (S) | — | 1.00 | 0.78 | 0.69 | 1.28 | 2.17 |
| Example 2 of the invention |  |  |  |  |  |  |  |
| base | (S) | — | 1.45 | 0.59 | 0.65 | 0.63 | 0.62 |
| hydrochloride | (S) | 1.59 | 0.42 | 0.33 | 0.48 | 0.51 | 0.56 |
| Comparative distomer* | (R) | +5.8 | +14.6 | +32.4 | +44.5 | +35.6 | +30.0 |

*% potentiating effects on bronchoconstriction statistically non-significant for 3.5 μmol/kg.

TABLE 3

Inhibitory effect, via the In.P. (intranasal-powder) route, on bronchoconstriction caused by 100 nmol/kg of histamine
test via the in.P. route (Results ED$_{50}$ μmol/kg)

| Compound | Config. | ED$_{50}$ at t = 5 min |
| --- | --- | --- |
| t = 5 min |  |  |
| Example 2 of the invention |  |  |
| base | (S) | 1.28 |
| hydrochloride | (S) | 1.77 |
| Cromakalim (INN) |  | 1.88 | test via the in.P. route (Results ED$_{50}$ μmol/kg)

The results of these tests demonstrate convincingly the inhibitory activity of the compounds of the invention with respect to ovalbumin- and histamine-induced bronchoconstriction in guinea pigs.

In addition, they demonstrate the specificity of the antihistaminic activity of the compounds of Examples 1 and 2 (S) configuration which are the subject of the invention.

Indeed, in comparison to their racemic (R,S) analogs, the compounds of the invention prove approximately at least twice as active.

Moreover, via the i.v. or In. route, the compounds of the invention show an activity equal to, if not greater than, the reference compounds with which they are compared.

More surprisingly, it is found that, as regards the product of Example 2 of the invention, both via the i.v. route and via the i.d. route, the corresponding distomer of (R) configuration shows, perceptibly though not significantly in statistical terms, a potentiating effect on histamine activity.

These anti-allergic, and in particular antihistaminic, properties in the bronchoconstriction test are seen not to be obvious from the standpoint of the teaching of the state of the art, and to be noteworthy from the standpoint of the observed dissociation of activity between the eutomers of formula (I) and their antipodes.

They justify the subject of the invention, which relates, by way of new products, to the enantiomers (I) of S configuration which are:

- (S)-(−)-N-allyl-2-amino-2-(3,4-dichlorobenzyl)-1-propanol,
- S-(+)-N-allyl-2-methylamino-2-(3,4-dichlorobenzyl)-1-propanol, and their salts, to a process for preparing them and to their use in the form of medicinal products intended for preventive or curative treatments of allergic states, in particular of those caused by histamine release.

In the form of suitable pharmaceutical compositions, the compounds of the invention, as a result of their anti-allergic activity, are useful in the treatment of asthmatic states, and in particular for inhibiting the bronchoconstriction or bronchospasm states of allergic asthma or of those resulting from acute or chronic bronchitis. The antihistaminic activity of the compounds justifies their application in the symptomatologies caused by histamine release, such as, for example, in allergies of the nasal and conjunctival mucosae, allergic rhinitis and certain forms of edema, of dermatosis, of pruritus or of eczema.

The low toxicity of the products permits the use of daily dosages of up to 1,000 mg, administered orally, in order to obtain the expected effects. They are usually, however, from 50 to 500 mg per day, administered orally, divided if necessary into several doses.

The products of the invention and their pharmaceutically acceptable salts are administered in the form of compositions appropriate to the routes which are suited to the nature and extent of the disorder to be treated.

These compositions are, for example, tablets, dragees, capsules, powders, suppositories, gels, suspensions or alternatively solutions to be injected or swallowed.

They are prepared by methods familiar to a person skilled in the art. They comprise from 1 to 50% by weight of active principle consisting of a compound (I) or one of its salts, and from 99 to 50% by weight of a pharmaceutically suitable vehicle which is compatible with the active principles and the physical form of the composition envisaged.

As non-limiting examples, the preparation of tablets and of injectable isotonic solution with the compounds of the invention is presented.

| Tablets | |
|---|---|
| Formula | |
| Active substance (I) according to Example 2 | 5 to 75 mg |
| Polyvinylpyrrolidone | 2 mg |
| Carboxymethylstarch | 8 mg |
| Magnesium stearate | 3 mg |
| Lactose | 60 to 76 mg |
| Monocrystalline cellulose | 122 to 76 mg |
| per tablet weighing 200 mg. | |
| Manufacture | |

Dissolve the polyvinylpyrrolidone in the proportion of 0.1 to 1.0% by weight in water, a low molecular weight alcohol such as ethanol or an aqueous-alcoholic mixture.

Separately, make an intimate mixture of the active substance, lactose and half the quantity of cellulose and of carboxymethylstarch, and wet this mixture with the solution obtained above.

Granulate the paste, dry the granules and size them on a sieve. Add the remainder of the components, mix intimately and then tablet on the basis of 200 mg per unit.

| Injectable isotonic solution | |
|---|---|
| Formula | |
| Active substance (I), hydrochloride of Example 2 | 10 mg |
| Sodium chloride | 9 mg |
| Distilled water q.s. | 1.0 ml |
| Manufacture | |

The solution is distributed in ampoules, which are sterilized by the usual thermal means after sealing; the solution can also be sterilized by filtration and distributed in ampoules which are then sealed, these operations being performed in a sterile atmosphere.

We claim:

1. (S)-(+)-N-allyl-2-methylamino-2-(3,4-dichlorobenzyl)-1-propanol hydrochloride.

2. A method of treating a human suffering from allergic or histamine-mediated diseases which comprises administering an anti-allergic effective amount of an enantiomer of (S) absolute configuration defined according to the Cahn-Ingold-Prelog rule and by formula (I):

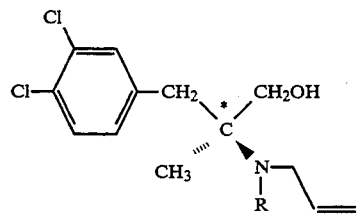

in which R is hydrogen or a methyl radical, or one of its addition salts with non-toxic acids.

3. The method of claim 2 which further comprises providing the enantiomer of Formula (I) in which R is hydrogen.

4. The method of claim 2 which further comprises providing the enantiomer of Formula (I) in which R is CH₃.

5. The method of one of claim 2–4 which further comprises administering the enantiomer in a dosage of from about 50 to about 1000 mg/day.

6. The method of claim 5 which further comprises administering the enantiomer as a pharmaceutical formulation comprising between about 1 and 50 percent by weight of the enantiomer and between about 99 and 50 percent by weight of a pharmaceutically acceptable vehicle which is compatible with the enantiomer.

7. The method of claim 6 which further comprises administering the enantiomer in the form of a tablet, dragee, capsule, powder, suppository, gel, suspension or solution.

8. The method of claim 6 which further comprises administering the enantiomer orally.

9. The method of claim 6 which further comprises administering the enantiomer by injection.

10. A process for preparing (S)-(−)-2-amino-2(3,4-dichlorobenzyl)-1-propanol of formula (II)

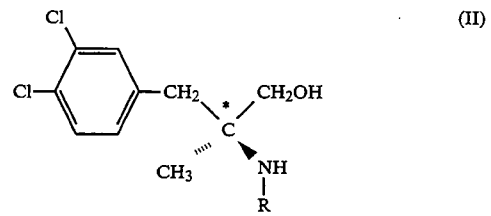

in which R is hydrogen, which comprises reacting 3,4-dichlorophenylacetone with a potassium cyanide and an ammonium carbonate to obtain (+/−)-5-3,4-dichlorobenzyl)-5-hydantoin; forming an addition salt by stereospecific salification of (+/−)-5-3,4-dichlorobenzyl)-5-hydantoin with (R)-(+)-α-methyl-benzylamine; treating the addition salt with acid to obtain (S)-(−)-5-(3,4-dichlorobenzyl)-5-methyl hydantoin in an alkaline aqueous solution to obtain (S)-(−)-2-amino-2-(3,4-dichlorobenzyl)alanine; and reducing the (S)-(−)-2-amino-2-(3,4-dichlorobenzyl) alanine with a borane-dimethyl sulfide complex to obtain the compound of formula (II).

11. The process of claim 10 which further comprises conducting the reaction between the 3,4-dichlorophenylacetone, the potassium cyanide and the ammonium carbonate in ethanol at a temperature of at least about 40° C.

12. The process of claim 10 which further comprises mixing the (+/−)-5-3,4-dichlorobenzyl)-5-hydantoin with water and a base to form a solution; adding (R)-(+)-α-methylbenzylamine to the solution; heating the solution to dissolve the reactants; and thereafter cooling the solution to form the addition salt.

13. The process of claim 10 which further comprises mixing the (S)-(−)-5-(3,4-dichlorobenzyl)-5-methyl hydantoin with a solution of sodium hydroxide with stirring and at a temperature of at least about 140° C. and at elevated pressure for a sufficient time to obtain (S)-(−)-2-amino-2-(3,4-dichlorobenzyl)alanine.

14. The process of claim 10 which further comprises reducing the (S)-(−)-2-amino-2-(3,4-dichlorobenzyl)alanine by adding it with the borane-dimethyl sulfide complex to tetrahydrofuran in the absence of moisture with stirring to form a solution; and gradually adding methanol and sodium hydroxide to form the compound of formula (II).

15. The process of claim 10 which further comprises conducting an N-allylation of the compound of formula (II) with an allyl halide to obtain an enantiomer of (S) absolute configuration defined according to the Cahn-Ingold-Prelog rule and by formula (I)

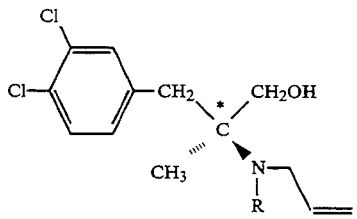

in which R is hydrogen.

16. The process of claim 15 which further comprises conducting the N-allylation of (S)-(−)-2-amino-2-(3,4-dichlorobenzyl)-1-propanol in an inert solvent.

17. The process of claim 16 which further comprises selecting the inert solvent to be toluene or acetonitrile.

18. The process of claim 16 which further comprises adding a basic agent to the inert solvent to promote the N-allylation reaction.

19. The process of claim 15 which further comprises selecting the allyl halide to be allyl chloride, allyl bromide or allyl iodide.

20. The process of claim 19 which further comprises utilizing about 0.5 to 1.5 mol of allyl halide per mole of amino alcohol and conducting the N-allylation reaction for about 1 to 24 hours at a temperature of about 20° to 110° C.

21. The process of claim 15 which further comprises utilizing about 0.5 to 1.5 mol of allyl bromide per mole of amino alcohol and conducting the N-allylation reaction for about 2 to 5 hours at a temperature about 40° to 100° C.

22. The process of claim 15 which further comprises conducting an N-methylation of the compound of formula (II) by reaction of formaldehyde and formic acid to obtain the enantiomer of formula (I) in which R is methyl.

23. The process of claim 22 which further comprises conducting the reductive methylation reaction in an aqueous formaldehyde solution which contains formic acid and provides about 1.2 to 3.5 mol of formaldehyde and about 2 and 5 mol of formic acid.

24. The process of claim 22 which further comprises initially reacting the formaldehyde exothermically with the compound of formula (I) to form a reaction product; adding the formic acid to the reaction product to form a mixture and heating the mixture for about 1 to 2 hours at about 90° to 100° C.

25. The process of claim 22 which further comprises purifying the enantiomer of formula (I) by a chromatographic method.

26. The process of claim 15 which further comprises purifying the enantiomer of formula (I) by a chromatographic method.

* * * * *